United States Patent
Hosoda et al.

(10) Patent No.: US 10,501,826 B2
(45) Date of Patent: Dec. 10, 2019

(54) SUPERELASTIC ALLOY

(71) Applicants: TANAKA KIKINZOKU KOGYO K.K., Chiyoda-ku, Tokyo (JP); TOKYO INSTITUTE OF TECHNOLOGY, Meguro-ku, Tokyo (JP)

(72) Inventors: Hideki Hosoda, Tokyo (JP); Tomonari Inamura, Tokyo (JP); Masaki Tahara, Tokyo (JP); Yuri Shinohara, Tokyo (JP); Kota Fuchiwaki, Tokyo (JP); Kenji Goto, Hiratsuka (JP)

(73) Assignees: TANAKA KIKINZOKU KOGYO K. K., Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 289 days.

(21) Appl. No.: 15/518,112

(22) PCT Filed: Oct. 14, 2015

(86) PCT No.: PCT/JP2015/079019
§ 371 (c)(1),
(2) Date: Apr. 10, 2017

(87) PCT Pub. No.: WO2016/063768
PCT Pub. Date: Apr. 28, 2016

(65) Prior Publication Data
US 2017/0314100 A1   Nov. 2, 2017

(30) Foreign Application Priority Data

Oct. 23, 2014 (JP) ................................ 2014-216449

(51) Int. Cl.
  C22C 14/00 (2006.01)
  C22F 1/00 (2006.01)
  C22F 1/18 (2006.01)
  A61L 31/00 (2006.01)

(52) U.S. Cl.
CPC .............. *C22C 14/00* (2013.01); *C22F 1/006* (2013.01); *C22F 1/183* (2013.01); *A61L 31/00* (2013.01); *A61L 2400/16* (2013.01); *C22F 1/00* (2013.01); *C22F 1/18* (2013.01)

(58) Field of Classification Search
CPC ..... A61L 2400/16; A61L 31/00; C22C 14/00; C22F 1/183
See application file for complete search history.

(56) References Cited

U.S. PATENT DOCUMENTS

| 5,927,345 A | * | 7/1999 | Samson | ................ | A61M 39/08 138/123 |
| 2002/0033717 A1 | * | 3/2002 | Matsuo | ................... | C22C 14/00 327/94 |
| 2009/0162243 A1 | * | 6/2009 | Diamant | ................. | A61L 29/02 420/580 |
| 2014/0338795 A1 | * | 11/2014 | Gloriant | ................... | C23C 8/24 148/217 |

FOREIGN PATENT DOCUMENTS

| JP | 2003-293058 A | 10/2003 |
| JP | 2004-124156 A | 4/2004 |
| JP | 2005-036273 A | 2/2005 |
| JP | 2006-089825 A | 4/2006 |
| JP | 2009-215650 A | 9/2009 |
| JP | 2014-152355 A | 8/2014 |
| WO | WO2013068691 | * 5/2013 |

OTHER PUBLICATIONS

Niinomi, M. et al. "Metallic biomaterials." 2008. Journal of artificial organs. 11. p. 105-110. (Year: 2008).*
EP, Extended European Search Report for EP application No. 15852424.9, dated May 29, 2018.
Shinohara et al., "Phase Constituents of Ti—Cr—Au and Ti—Cr—Au—Zr Alloy Systems," Materials Science Forum, vols. 654-656, Jun. 30, 2010, pp. 2122-2125.
PCT, International Search Report for PCT/JP2015/079019, dated Jan. 12, 2016.

* cited by examiner

*Primary Examiner* — Colleen P Dunn
*Assistant Examiner* — Nicholas A Wang
(74) *Attorney, Agent, or Firm* — Orrick, Herrington & Sutcliffe LLP; Joseph A. Calvaruso; K. Patrick Herman

(57) ABSTRACT

The present invention provides a superelastic alloy containing Au in an amount of 8.0% by mass or more and 20.0% by mass or less and at least one of Cr and Mo as essential additive elements, Ta as an optional additive element, and Ti and inevitable impurities as a balance, wherein the Cr equivalent calculated on the basis of the following formula for the relationship of the Cr content, the Mo content and the Ta content is within the range of more than 0.5 and less than 8.0. The alloy is a Ni-free superelastic alloy, and has favorable X-ray-imaging property. Accordingly, the alloy can be suitably used in medical fields.

Cr equivalent=[Cr content (% by mass)]+([Mo content (% by mass)]/1.7)+([Ta content (% by mass)]/15)    [Formula 1]

10 Claims, No Drawings

SUPERELASTIC ALLOY

TECHNICAL FIELD

The present invention relates to a superelastic alloy, and particularly to a superelastic alloy which is capable of exhibiting superelasticity in a normal temperature region while being Ni-free and which has excellent X-ray-imaging property.

BACKGROUND ART

A superelastic alloy has a much wider elastic range than other metal materials at a temperature equal to or higher than the reverse transformation temperature, and immediately recovers an original shape even when deformed. The superelastic alloy is an alloy material which is expected to be applied to medical fields and medical devices such as orthodontics tools, catheters, stents, bone plates, coils, guide wires and clips by virtue of the above-mentioned property.

Studies on superelastic alloys are conducted with various kinds of alloy systems on the basis of knowledge about shape memory alloys. Superelastic alloys that are currently most well known in terms of practical use include Ni—Ti-based shape memory alloys. Ni—Ti-based shape memory alloys have a reverse transformation temperature of 100° C. or lower, can exhibit superelasticity at the body temperature of a human being, and therefore may be qualitatively applicable to medical devices. However, Ni—Ti-based shape memory alloys contain Ni for which there is a concern about biocompatibility which is associated with metal allergy. Biocompatibility is a matter that may be fetal when application to medical fields is considered.

Thus, alloy materials which can exhibit superelastic property while being Ni-free have been developed. For example, Patent Document 1 discloses a Ti alloy obtained by adding Mo and one of Al, Ga and Ge to Ti. In the Ti alloy, Mo is added as an additive element having an action of stabilizing the $\beta$ phase of Ti, and Al, Ga or Ge that acts to stabilize the $\alpha$ phase of Ti is added while consideration is given to the biocompatibility of each additive element, and the contents of these additive elements are optimized to exhibit superelastic property. Additionally, it has been reported that various kinds of Ti-based alloys such as Ti—Nb—Al alloys and Ti—Nb—Sn alloys can exhibit superelastic property.

RELATED ART DOCUMENT

Patent Documents

Patent Document 1: JP 2003-293058 A
Patent Document 2: JP 2005-36273 A
Patent Document 3: JP 2004-124156 A

SUMMARY OF THE INVENTION

Problems to be Solved by the Invention

Superelastic materials including conventional Ti alloys as described above can exhibit superelastic property while excluding Ni, and are therefore expected to be used in medical fields, but still have many points to be improved.

Specifically, in use of various kinds of medical devices as described above, X-ray imaging is often required for examination of installation and working conditions of the medical devices. For example, in treatment with a stent, an operation is often performed while examination is conducted with an X-ray for determining whether the device moves to and arrives at an operation region. Thus, the quality of X-ray-imaging property may affect the result of an operation. In this respect, some of the above-mentioned superelastic materials are poor in X-ray-imaging property.

An object of the present invention is to provide an alloy material which has excellent superelastic property while being Ni-free and has favorable x-ray-imaging property, and which is sufficiently applicable to medical fields.

Means for Solving the Problems

In the above-mentioned conventional superelastic alloy (Patent Document 1), various kinds of additive elements are added to Ti to stabilize a $\beta$ phase serving as a parent phase of the superelastic alloy. While referring to the directivity of the conventional art, the present inventors selected additive elements based on an approach corresponding to the object of the present application. Specifically, Au was first selected as an essentially additive element to Ti for securing X-ray-imaging property. Au is a heavy metal having a large atomic weight, has favorable X-ray-imaging property, and is a metal element having excellent biocompatibility. Further, Au is an element capable of contributing to exhibition of diffusion-less transformation that forms the basis of a superelastic phenomenon.

Of course, addition of Au alone does not cause exhibition of a superelastic phenomenon. When the Au content of a Ti—Au-based alloy is increased, a shape memory phenomenon is exhibited, but the reverse transformation temperature increases, and thus exhibition of superelasticity in a normal temperature range cannot be expected. The present inventors extensively conducted studies for setting the addition amount of Au to Ti within an appropriate range, and also finding other additive elements capable of stabilizing a $\beta$ phase in this state, and thus arrived at the present invention.

The present invention provides a superelastic alloy containing Au in an amount of 8.0% by mass or more and 20.0% by mass or less and at least one of Cr and Mo as essential additive elements, Ta as an optional additive element, and Ti and inevitable impurities as a balance, wherein the Cr equivalent calculated on the basis of the following formula for the relationship of the Cr content, the Mo content and the Ta content is within the range of more than 0.5 and less than 8.0.

$$\text{Cr equivalent} = [\text{Cr content (\% by mass)}] + ([\text{Mo content (\% by mass)}]/1.7) + ([\text{Ta content (\% by mass)}]/15) \quad [\text{Formula 1}]$$

As described above, the Ti—Au-based superelastic alloy according to the present invention is a Ti-based alloy which essentially contains Au and Cr and/or Mo, and further contains Ta as necessary, and thus the alloy can exhibit superelastic property. Hereinafter, the configuration of the superelastic alloy according to the present invention will be described in terms of the actions of the additive elements (Au, Cr, Mo and Ta) and the contents of these elements. Ti is a metal element being a main component that forms the balance of the Ti—Au-based superelastic alloy according to the present invention. Ti is a metal that forms the parent phase ($\beta$ phase) of the alloy. The superelastic alloy according to the present invention may contain inevitable impurities as elements other than Ti and the additive elements.

I: Actions of Additive Elements

First, the actions of Au, Cr and Mo as essential additive elements and Ta as an optional additive element will be described.

(i) Au (Essential Additive Element)

Au exhibits an X-ray imaging action as a heavy metal atom. Further, Au has an action of causing diffusionless transformation by retarding atomic diffusion of metal atoms that form the alloy, and therefore Au can contribute to exhibition of a superelastic phenomenon.

(ii) Cr and Mo (Essential Additive Elements)

Cr and Mo are elements having an action of stabilizing a β phase being the parent phase of the alloy, and these elements are additive elements that are essential for exhibition of superelasticity at room temperature. Both Cr and Mo may be added, but addition of only one of these elements can contribute to exhibition of superelasticity. Cr and Mo both have a β phase stabilizing action, but in this action, Cr has a higher effect, and can contribute to stabilization of a β phase, and hence exhibition of superelasticity with a smaller amount as compared to Mo.

(iii) Ta (Optional Additive Element)

In the present invention, Ta is optionally added in addition to Cr or Mo. Similarly to Cr and Mo, Ta has an action of stabilizing a β phase, and contributes to exhibition of superelasticity. Of course, Ta has a lower effect than Cr and Mo in this action. Ta is a heavy metal (molecular weight: 180.9) similar to gold, and therefore X-ray-imaging property can be secured by adding Ta. The superelastic alloy according to the present invention has a reduced Au content as compared to a conventional Ti—Au-based binary alloy, and reduction of the Au content deteriorates X-ray-imaging property. Addition of Ta is useful for securing x-ray-imaging property in this case. Note that addition of Ta is optional rather than being essential.

II: Contents of Additive Elements

The contents of the above-mentioned additive elements: Au, Cr, Mo and Ta will now be described.

(i) Content of Au

First, the content of Au is 8.0% by mass or more and 20.0% by mass or less. When the Au content is less than 8.0% by mass, superelasticity property is not exhibited. Further, X-ray-imaging property is deteriorated. When the Au content is more than 20.0% by mass, a hard intermetallic compound containing Au, such as $Ti_3Au$, is easily formed, and accordingly the material tends to be embrittled. The Au content is more preferably 9% by mass or more and 16% by mass or less.

(ii) Contents of Cr, Mo and Ta

The contents of the additive elements: Cr, Mo and Ta are determined in consideration of the action (β phase stabilizing action) exhibited by these elements. Specifically, the Cr equivalent calculated on the basis of the contents of the elements from the following formula is required to be within a predetermined range.

$$\text{Cr equivalent} = [\text{Cr content (\% by mass)}] + ([\text{Mo content (\% by mass)}]/1.7) + ([\text{Ta content (\% by mass)}]/15) \quad \text{[Formula 1]}$$

The "Cr equivalent" is a term defined in the present invention. In the Cr equivalent, the levels of the β phase stabilizing actions of Cr, Mo and Ta are considered, the effects of Mo and Ta are quantified based on the effect of Cr (Cr equivalent=1) having the highest effect, and the effects of these elements are added up to show a superelasticity exhibiting effect. In the present invention, the Cr equivalent is required to be more than 5.0 and less than 8.0. An alloy having a composition in which the Cr equivalent is 5.0 or less, or the Cr equivalent is 8.0 or more does not exhibit superelasticity. The contents of Cr, Mo and Ta as additive elements may be adjusted so that the Cr equivalent is more than 5.0 and less than 8.0 as described above.

In the present invention, both Cr and Mo can be simultaneously added, so that the essential additive elements include Au, Cr and Mo. Here, the Cr equivalent is calculated on the basis of the contents of Cr and Mo, and the Cr equivalent is made to fall within the range of more than 5.0 and less than 8.0. Here, the content of Cr is preferably 0.1% by mass or more, and the content of Mo is preferably 0.1% by mass or more.

In the present invention, one of Cr and Mo can be selected, and added. When Cr is selected, the essential additive elements include Au and Cr. As described above, addition of Cr is most effective for the β phase stabilizing action. The Cr content here is preferably 4.0% by mass or more. The upper limit of the Cr content is less than 8.0% by mass from the definition of the Cr equivalent. Here, addition of Ta is optional.

When Mo is selected, the essential additive elements include Au and Mo, and the content of Mo is preferably 6.8% by mass or more, which is higher than the content of Cr. The content of Mo is less than 13.6% by mass from the definition of the Cr equivalent. Here, addition of Ta is optional.

The content of Ta is preferably 20% by mass or less. Note that the lower limit of the content of Ta is 0% by mass because Ta is an optional additive element. The content of Ta is more preferably 9% by mass or more and 16% by mass or less.

(iii) Alloy Composition Considering Properties Other than Superelasticity

In the present invention, the contents of the additive elements are defined on the basis of the Cr equivalent for exhibition of superelasticity as described above. The contents of the additive elements can be adjusted in consideration of properties such as processability in addition to exhibition of superelasticity. In the present invention, the ratio of the sum of the Ta content and the Ti content to the Au content ([Au content (%)]/[Ta content (%)]+[Ti content (%)]) is preferably less than 0.29. The superelastic alloy according to the present invention is based on a Ti—Au alloy, and in this system, an intermetallic compound ($Ti_3Au$) of Au and Ti may be produced. The superelastic alloy according to the present invention may contain Ta, and Ta may also form an intermetallic compound ($Ta_3Au$) with Au. These intermetallic compounds are brittle, and therefore when they are excessively deposited, processability may be impaired. Preferably, the ratio of the sum of the Ta content and the Ti content to the Au content is regulated to secure processability of the alloy.

Further, the superelastic alloy according to the present invention is preferably one in which the sum of the Au content and the Ta content ([Au content (%)]+[Ta content (%)]) is 8.0% by mass or more and 40.0% by mass or less. This is because Au and Ta, which are heavy metal atoms, are additive elements that improve the X-ray-imaging property of the alloy. Note that when the sum of the Au content and the Ta content is more than 40.0% by mass, superelasticity is not exhibited.

The superelastic alloy according to the present invention can be produced by a usual melting/casting method, but it is preferable to heat-treat the alloy after casting. The heat-treatment is intended for adjusting the distribution state of an intermetallic compound ($Ti_3Au$ or $Ta_3Au$) in the alloy to stably exhibit superelastic phenomenon. Preferably, this heat treatment is performed by heating and holding the alloy at 700 to 900° C. for 0.1 to 6 hours.

Advantageous Effects of the Invention

As described above, the superelastic alloy according to the present invention is an alloy capable of exhibiting superelasticity at normal temperature while being Ni-free. The superelastic alloy also has favorable processability. The superelastic alloy according to the present invention is in the form of a quinary alloy: Ti—Au—Cr—Mo—Ta alloy, a quaternary alloy: Ti—Au—Cr—Ta alloy or Ti—Au—Mo—Ta alloy, or a ternary alloy: Ti—Au—Cr alloy or Ti—Au—Mo alloy. The contents of Cr, Mo and Ta are adjusted on the basis of the Cr equivalent to suitably exhibit superelasticity.

The superelastic alloy according to the present invention has favorable biocompatibility, and also has favorable X-ray-imaging property because the superelastic alloy contains heavy metals: Au and Ta as constituent elements. Owing to the above-mentioned features, the present invention can be expected to be applied to medical devices, specifically orthodontics tools, artificial dental roots, clips, staples, catheters, stents, bone plates and so on.

DESCRIPTION OF EMBODIMENT

Hereinafter, an embodiment of the present invention will be described. In this embodiment, Ti—Au-based alloys were produced while the contents of constituent elements were changed, and presence/absence of superelastic property in a normal temperature range, and X-ray-imaging property were evaluated.

For preparation of various kinds of superelastic alloys as samples, 99.99% by mass of Ti, 99.95% by mass of Au, 99.9% by mass of Cr, 99.99% by mass of Mo and 99.99% by mass of Ta were used as melting raw materials. Using a non-consumable W electrode-type argon arc melting furnace, these raw materials were melted in an Ar-1% H2 atmosphere to produce an alloy ingot (thickness: 1 to 2 mm).

Next, the produced alloy ingot was heat-treated. In this heat treatment, the alloy ingot was heated at 800° C. (1073 K) for 30 minutes, and then cooled with water. The treated alloy ingot was subjected to discharge processing to prepare tension test pieces (thickness: 0.2 mm, width: 2 mm and length: 20 mm (length of measurement section: 10 mm)).

For the alloy test pieces produced as described above, first a tension test (stress loading-unloading test) was conducted, and superelastic property was evaluated. In the tension test for evaluation of superelasticity, the test piece was loaded at $5 \times 10^{-4}$/second in the air (room temperature) until it was elongated by 4%, the test piece was then unloaded, and a residual strain was measured to determine a recovery ratio (superelastic shape recovery ratio). The superelastic shape recovery ratio was determined from the following formula.

superelastic shape recovery ratio (%)=2% deformation plastic strain (%)−residual strain (%)/2% deformation plastic strain×100   [Formula 2]

The "plastic strain" is a value obtained by subtracting an elastic deformation strain from a total deformation strain.

When the calculated recovery ratio was 50% or more, it was determined that superelasticity was exhibited (passing: "○"). Samples having a recovery ratio of 80% or more were rated very good ("⊙").

In the test for evaluation of superelastic property, the behavior of the test piece after unloading was observed from the middle of deformation, and processability was evaluated. Samples fractured during deformation were evaluated as having low processability, and marked as "FRC (Fracture)". For other behaviors, samples exhibiting only elastic recovery after deformation/unloading (i.e. samples that did not exhibit superelasticity) were recorded as "EL (Elasticity)". Further, samples exhibiting only elastic recovery after deformation/unloading were heated, and samples exhibiting shape recovery when heated were recorded as "SME (Shape Memory Effect)". Samples exhibiting a superelastic phenomenon (recovery ratio: 50%) were recorded as "SE (Superelasticity)".

Further, X-ray-imaging property was examined for the test pieces. In this test, the ingot was sandwiched between two acrylic plates from above and below, placed in an X-ray blood vessel imaging device, and irradiated with an X-ray under conditions used in actual X-ray diagnosis (tube voltage: 60 to 125 kV, tube current: 400 to 800 mA, irradiation time: 10 to 50 msec, using an Al filter (2.5 mm)). The obtained transmission image was visually observed. Samples, the sample shape of which was clearly seen, were rated "○", and samples, the sample shape of which was not as clear as that for TiNi, were rated "×".

The results of evaluating superelastic property and X-ray-imaging property for the test pieces as described above are shown in Table 1.

| | Composition (wt%) | | | | | | Au + Ta | Evaluation results | | |
| | | | | | | | | Superelasticity | | X-ray |
| | Au | Cr | Mo | Ta | Ti | Cr equivalent | Au/(Ti + Ta) | (%) | Behavior[*1] | Recovery ratio[*2] | imaging property |
|---|---|---|---|---|---|---|---|---|---|---|---|
| Example 1 | 9.99 | 4.39 | — | 15.21 | Balance | 5.41 | 0.12 | 25.19 | SE | ⊙ | ○ |
| Example 2 | 12.71 | 4.19 | — | 17.42 | | 5.36 | 0.15 | 30.13 | SE | ⊙ | ○ |
| Example 3 | 12.99 | 4.29 | — | 14.83 | | 5.27 | 0.15 | 27.82 | SE | ⊙ | ○ |
| Example 4 | 13.28 | 4.38 | — | 12.13 | | 5.19 | 0.16 | 25.41 | SE | ⊙ | ○ |
| Example 5 | 13.58 | 4.48 | — | 9.31 | | 5.10 | 0.17 | 22.88 | SE | ○ | ○ |
| Example 6 | 15.84 | 4.18 | — | 14.48 | | 5.15 | 0.20 | 30.32 | SE | ○ | ○ |
| Example 7 | 12.45 | 4.11 | — | 19.90 | | 5.43 | 0.15 | 32.35 | SE | ○ | ○ |
| Example 8 | 12.98 | 5.14 | — | 14.82 | | 6.13 | 0.16 | 27.80 | SE | ○ | ○ |
| Example 9 | 14.56 | 5.77 | — | — | | 5.77 | 0.18 | 14.56 | SE | ○ | ○ |
| Example 10 | 14.55 | 6.72 | — | — | | 6.72 | 0.18 | 14.55 | SE | ○ | ○ |
| Example 11 | 14.54 | 7.68 | — | — | | 7.68 | 0.19 | 14.54 | SE | ○ | ○ |
| Example 12 | 12.53 | — | 7.63 | 14.32 | | 5.44 | 0.16 | 26.85 | SE | ○ | ○ |
| Comparative Example 1 | 7.71 | 5.09 | — | — | Balance | 5.09 | 0.09 | 7.71 | EL | x | x |
| Comparative Example 2 | 20.67 | 7.28 | — | — | | 7.28 | 0.29 | 20.67 | FRC | — | ○ |
| Comparative Example 3 | 26.25 | 4.33 | — | — | | 4.33 | 0.38 | 26.25 | FRC | — | ○ |

-continued

|  | Composition (wt%) | | | | | Cr equivalent | Au/(Ti + Ta) | Au + Ta (%) | Superelasticity Behavior*1 | Recovery ratio*2 | X-ray imaging property |
|---|---|---|---|---|---|---|---|---|---|---|---|
|  | Au | Cr | Mo | Ta | Ti | | | | | | |
| Comparative Example 4 | 8.43 | — | — | 57.76 | Balance | 3.85 | 0.09 | 66.19 | EL | x | ○ |
| Comparative Example 5 | 9.82 | — | — | 44.84 | | 2.99 | 0.11 | 54.66 | SME | x | ○ |
| Comparative Example 6 | 13.15 | — | — | 50.07 | | 3.34 | 0.15 | 63.22 | EL | x | ○ |
| Comparative Example 7 | 11.95 | 3.94 | — | 24.56 | Balance | 5.58 | 0.14 | 36.51 | EL | x | ○ |
| Comparative Example 8 | 13.00 | 3.43 | — | 14.84 | | 4.42 | 0.16 | 27.84 | SME | x | ○ |
| Comparative Example 9 | 14.52 | 9.58 | — | — | | 9.58 | 0.19 | 14.52 | EL | x | ○ |
| Comparative Example 10 | 7.72 | 3.06 | — | — | Balance | 3.06 | 0.09 | 7.72 | EL | x | x |
| Comparative Example 11 | 7.69 | 8.12 | — | — | | 8.12 | 0.09 | 7.69 | EL | x | x |
| Comparative Example 12 | 7.68 | 10.14 | — | — | | 10.14 | 0.09 | 7.68 | EL | x | x |
| Comparative Example 13 | 26.16 | 8.63 | — | — | | 8.63 | 0.34 | 26.16 | FRC | — | ○ |
| Comparative Example 14 | 14.57 | 4.81 | — | — | Balance | 4.81 | 0.18 | 14.57 | SME | x | ○ |
| Comparative Example 15 | 14.23 | 4.69 | — | 3.25 | | 4.91 | 0.17 | 17.48 | SME | x | ○ |
| Comparative Example 16 | 13.90 | 4.58 | — | 6.30 | | 5.00 | 0.17 | 20.24 | SME | x | ○ |
| Comparative Example 17 | 12.83 | — | 3.12 | 14.65 | Balance | 3.06 | 0.15 | 27.48 | SME | x | ○ |
| Comparative Example 18 | 14.01 | — | 8.50 | — | | 5.00 | 0.19 | 14.01 | SME | x | ○ |
| Comparative Example 19 | 12.25 | — | 12.03 | 13.99 | | 8.00 | 0.13 | 26.25 | EL | x | ○ |
| Comparative Example 20 | 11.98 | — | 16.04 | 13.69 | | 10.35 | 0.17 | 25.67 | EL | x | ○ |

*1: Behaviors
ERC: ruptured during deformation
EL: exhibiting only elastic recovery after deformation
SME: exhibiting elastic recovery after deformation, and further exhibiting shape recover when heated
SE: exhibiting superelasticity (exhibiting nonlinear shape recovery after unloading)
*2: Recovery ratio evaluation criteria
—: ruptured, and measurement impossible
x: not exhibiting nonlinear recovery by superelasticity
○: recovery ratio after 4% deformation is 50% or more and less than 80%
⊙: recovery ratio after 4% deformation is 80% or more Table 1 shows that the Ti—Au-based alloys of examples exhibited a superelastic phenomenon (Examples 1 to 12).

The relationship of the constituent elements were minutely examined, and the result showed that the alloys of Comparative Examples 1 to 3 in which the Au content fell out of the required range did not exhibit superelasticity. The alloys of Comparative Examples 2 and 3 were ruptured during deformation (FRC), and were thus supposed to have low processability. This may be because the Au content was extremely high, so that an intermetallic compound ($Ti_3Au$) was excessively produced. The alloy of Comparative Example 1 which has a low Au content is poor in X-ray-imaging property.

The results from Comparative Examples 4 to 6 show that addition of a β phase stabilizing element: Cr or Mo is absolutely necessary for exhibition of superelasticity. Of course, addition of Cr does not always result in exhibition of superelasticity. When Cr is added, the addition amount of Cr is preferably set to 4% by mass or more, and also the Cr equivalent is considered (Comparative Examples 7 to 9).

In the alloys of Comparative Examples 10 to 13, the Au content and the Cr content each fall out of the required range, and thus these alloys do not exhibit superelasticity. However, the results from Comparative Examples 14 to 16 show that if the Cr equivalent falls out of the required range, superelasticity is not exhibited even when both the Au content and the Cr content are within the required range. Accordingly, a composition formulation considering the Cr equivalent is required. Regarding the Cr equivalent, the Cr equivalent in each of Comparative Examples 16 and 18 is 5.0, a value that lies just on the borderline in the invention of the present application. The alloys of Comparative Examples 16 and 18 do not exhibit superelasticity, but have a shape memory effect (SME). Accordingly, it is supposed that in the alloy system of the invention of the present application, the threshold of the Cr equivalent is 5.0.

Regarding the actions of Cr and Mo, it was confirmed that the alloy of Example 12 contained Mo in place of Cr, but exhibited superelasticity. Note that consideration of the Cr equivalent is required in addition of Mo (Comparative Examples 17 to 20). Ta is an optional additive element. It was confirmed that even when Ta was not added, superelasticity was exhibited (Examples 9 to 11).

INDUSTRIAL APPLICABILITY

The elastic alloy according to the present invention does not contain Ni, and therefore has biocompatibility. Moreover, the elastic alloy can exhibit a superelastic phenomenon. This alloy contains Au and Ta, and therefore has favorable X-ray-imaging property, and thus application of the alloy to various kinds of medical devices can be expected.

The invention claimed is:

1. A superelastic alloy containing Au in an amount of 8.0% by mass or more and 20.0% by mass or less, Ta in an amount of 9.0% by mass or more and 20.0% by mass or less, either Cr or Mo as additive elements, and Ti and inevitable impurities as a balance, wherein
    a Cr equivalent calculated on a basis of Formula 1 for a relationship of a Cr content, a Mo content and a Ta content is within the range of more than 0.5 and less than 8.0;

Cr equivalent=[Cr content (% by mass)]+([Mo content (% by mass)]/1.7)+([Ta content (% by mass)]/15)      [Formula 1]

and wherein the superelastic alloy contains $Ti_3Au$ and $Ta_3Au$ intermetallic compounds and has a superelastic shape recovery ratio of 50% or more calculated on a basis of Formula 2 when subjected to a tension test and unloaded residual strain:

superelastic shape recovery ratio (%)=2% deformation plastic strain (%)–residual strain (%)/2% deformation plastic strain×100    [Formula 2]

wherein the plastic strain is a value obtained by subtracting an elastic deformation strain from a total deformation strain.

2. The superelastic alloy according to claim 1, wherein the additive elements include Au, Cr, and Ta, and the Cr content is 4.0% by mass or more.

3. The superelastic alloy according to claim 1, wherein the additive elements include Au, Mo, and Ta, and the Mo content is 6.8% by mass or more.

4. The superelastic alloy according to claim 1, wherein a ratio of a sum of the Ta content and the Ti content to the Au content ([Au content (% by mass)]/[Ta content (% by mass)]+[Ti content (% by mass)]) is less than 0.29.

5. The superelastic alloy according to claim 1, wherein the sum of the Au content and the Ta content ([Au content (% by mass)]+[Ta content (% by mass)] is 8.0% by mass or more and 40.0% by mass or less.

6. The superelastic alloy according to claim 2, wherein a ratio of a sum of the Ta content and the Ti content to the Au content ([Au content (% by mass)]/[Ta content (% by mass)]+[Ti content (% by mass)]) is less than 0.29.

7. The superelastic alloy according to claim 3, wherein a ratio of a sum of the Ta content and the Ti content to the Au content ([Au content (% by mass)]/[Ta content (% by mass)]+[Ti content (% by mass)]) is less than 0.29.

8. The superelastic alloy according to claim 2, wherein the sum of the Au content and the Ta content ([Au content (% by mass)]+[Ta content (% by mass)] is 8.0% by mass or more and 40.0% by mass or less.

9. The superelastic alloy according to claim 3, wherein the sum of the Au content and the Ta content ([Au content (% by mass)]+[Ta content (% by mass)] is 8.0% by mass or more and 40.0% by mass or less.

10. The superelastic alloy according to claim 4, wherein the sum of the Au content and the Ta content ([Au content (% by mass)]+[Ta content (% by mass)] is 8.0% by mass or more and 40.0% by mass or less.

* * * * *